United States Patent
McCarthy et al.

[11] Patent Number: 5,349,953
[45] Date of Patent: Sep. 27, 1994

[54] PHOTOPLETHYSMOGRAPHICS USING COMPONENT-AMPLITUDE-DIVISION MULTIPLEXING

[75] Inventors: Rex McCarthy, Newbury Park; Robert Smith, Corona, both of Calif.

[73] Assignee: Sensormedics, Corp., Yorba Linda, Calif.

[21] Appl. No.: 665,595

[22] Filed: Mar. 5, 1991

[51] Int. Cl.$^5$ ............................................. A61B 5/00
[52] U.S. Cl. .................................. 128/633; 128/666; 364/413.03
[58] Field of Search .............................. 128/633–634, 128/664–666; 356/39–41; 251/335

[56] References Cited

U.S. PATENT DOCUMENTS 4,653,498  3/1987  New, Jr. et al. ............... 128/689
4,908,762  3/1990  Suzuki et al. .................. 128/633

FOREIGN PATENT DOCUMENTS 8804155  6/1988  World Int. Prop. O. .......... 128/666

Primary Examiner—Lee S. Cohen
Assistant Examiner—Robert L. Nasser, Jr.
Attorney, Agent, or Firm—Lyon & Lyon

[57] ABSTRACT

A plurality of carrier signals, distinguishable by amplitudes of signal components (e.g., frequency components), are respectively applied to a plurality of energy emitters (e.g., infrared and red light emitters). A detector receives the sum of the energy after modulation at each emitter wavelength, e.g. by blood tissue of a patient. An output of the detector is then demultiplexed, whereby a component of modulation at each emitter wavelength may be determined. The carrier signals may comprise time-varying periodic signals with identical frequency and frequency components, such as mixtures of identical sets of pure sine waves. When the number of signal components exceeds the number of emitter wavelengths, sufficient information is provided during demultiplexing to detect and correct errors introduced by ambient light sources and other interference.

44 Claims, 3 Drawing Sheets

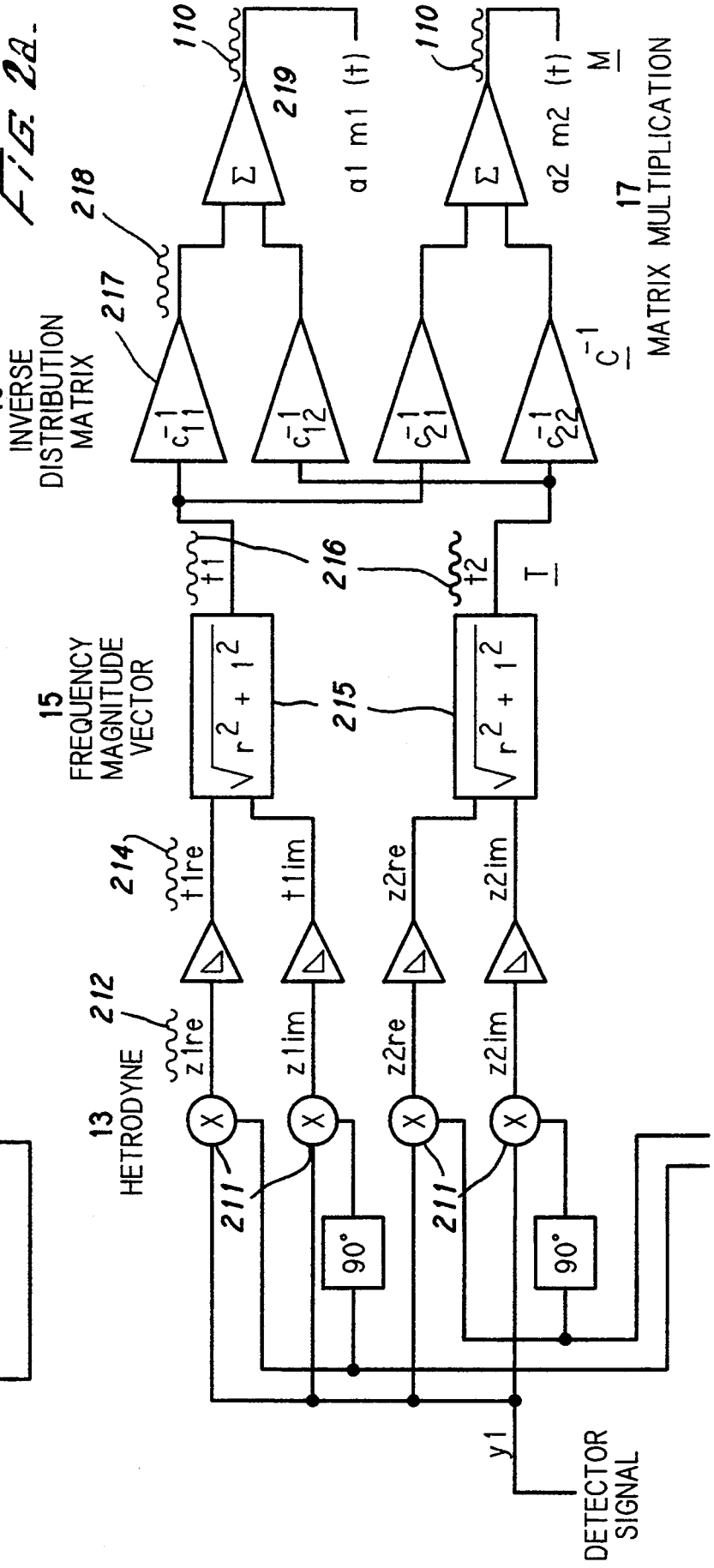

PHOTOPLETHYSMOGRAPHICS USING COMPONENT-AMPLITUDE-DIVISION MULTIPLEXING

BACKGROUND OF THE INVENTION

1. Field of the Invention

This invention relates to photoplethysmographics. More specifically, this invention relates to component-amplitude-division multiplexing and demultiplexing of signals for infrared and red absorption of blood.

2. Description of Related Art

It is well known in the art to collect photoplethysmographic data simultaneously at a plurality of energy wavelengths. For example, blood oxygen concentration may be measured by determining absorption by a patient's tissues on infrared and red light; the degree of absorption is typically different for these two wavelengths. Infrared and red light are emitted into the patient's tissues (e.g., by infrared and red LEDs) and the total energy received to be detected by a single detector (e.g., a photodiode). However, one problem is that the signal produced by the detector must be processed to separate the infrared and portions from each other.

One method of the prior art is shown in U.S. Pat. No. 4,407,290. Time-division multiplexing is used to alternately switch on the infrared and red emitters, at a frequency greater than the patient's pulse rate. The detector signal is then separated into infrared and red portions by sampling in synchrony with the on/off switching of the infrared and red emitters.

While this method successfully separates the infrared and red portions, it generally requires that sampling the detector signal must be synchronized with the on/off switching of the infrared and red emitters. It is also difficult while using this method to compensate for noise sources such as ambient light and electromagnetic interference.

A second method of the prior art is shown in U.S. Pat. No. 4,800,885. The infrared and red emitters are driven at two different frequencies. The detector signal is then separated into infrared and red portions by filtering at those two different frequencies.

While this method successfully separates the infrared and red portions, the method described in the patent requires demultiplexing signals which are phase-synchronized with the multiplexing frequencies, and produces a higher power output than the time-division multiplexing method. Also, while this method may avoid noise sources at predetermined and known frequencies, it is difficult to compensate for noise sources which were not known before the multiplexing frequencies were chosen.

SUMMARY OF THE INVENTION

The invention provides a method of multiplexing and demultiplexing of signals, called "component-amplitude-division" herein, which may be applied to measuring blood tissue absorption at infrared and red wavelengths. A plurality of carrier signals, distinguishable by amplitudes of signal components (e.g., frequency components), are respectively applied to a plurality of energy emitters (e.g., infrared and red emitters). A detector receives the sum of the energy after modulation at each emitter wavelength, e.g. by blood tissue of a patient. An output of the detector is then demultiplexed, whereby a component of modulation at each emitter wavelength may be determined.

In a preferred embodiment, the carrier signals may comprise time-varying periodic signals with identical frequency and frequency components, such as mixtures of identical sets of pure sine waves. For example, in a preferred embodiment, a first carrier $\alpha$ may comprise a mixture of two sine waves $\alpha 1w1 + \alpha 2w2$, while a second carrier may comprise a different mixture of the same two sine waves $\beta 1w1 + \beta 2w2$. Alternatively, $\beta$ may comprise a mixture of three sine waves $\alpha 1w1 + \alpha 2w2 + \alpha 3w3$, while $\beta$ may comprise a different mixture of the same three sine waves $\beta 1w1 + \beta 2w2 + \beta 3w3$. When the number of signal components exceeds the number of emitter wavelengths, sufficient information is provided during demultiplexing to detect and correct errors introduced by ambient light sources and other interference.

DESCRIPTION OF THE PREFERRED EMBODIMENT

An embodiment of this invention may be used together with inventions which are disclosed in a copending application titled "PHOTOPLETHYSMOGRAPHICS USING ENERGY-REDUCING WAVEFORM SHAPING", application Ser. No. 07/664,782, Lyon & Lyon, filed the same day in the name of the same inventors, hereby incorporated by reference as if fully set forth herein.

Photoplethysmographic System

Figure 1:
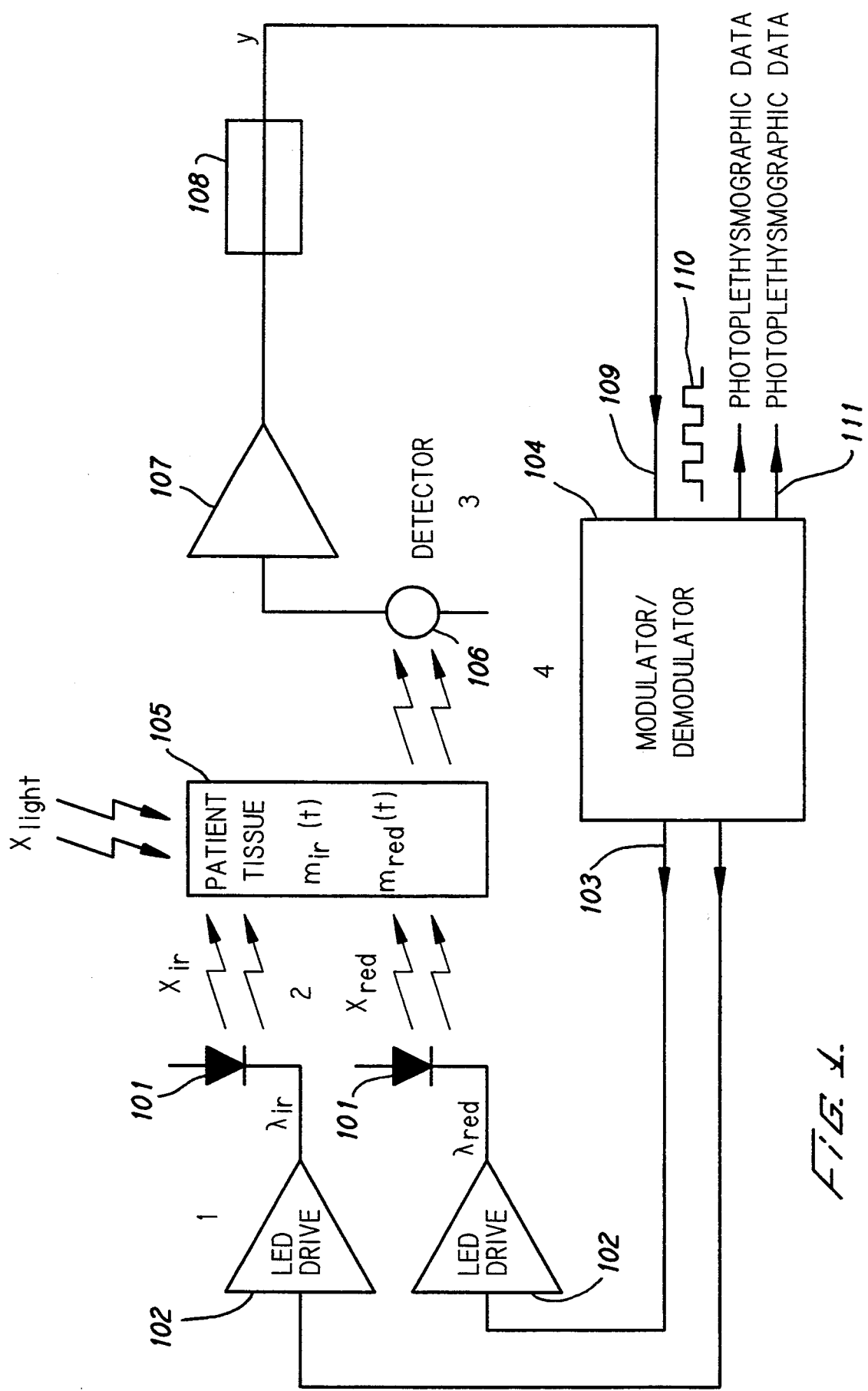
FIG. 1 shows a block diagram of a photoplethysmographic system comprising an embodiment of the invention.

FIG. 1 shows a block diagram of a photoplethysmographic system comprising an embodiment of the invention.

A plurality of energy emitters 101 may each be tuned to a separate wavelength. In a preferred embodiment for measuring blood oxygen, one of the emitters 101 may comprise an infrared light emitter and may operate at a wavelength of about 880 nanometers; another one of the emitters 101 may comprise red light emitter and may operate at a wavelength of about 656 nanometers. (As used herein, "light" refers to electromagnetic energy of any wavelength, whether visible or not.) However, it may occur that other wavelengths may be useful, such as for measuring blood carbon dioxide, blood carbon monoxide, other blood gas concentrations, blood glucose, or more generally, other chemical and/or physical concentrations.

Figure 2B:
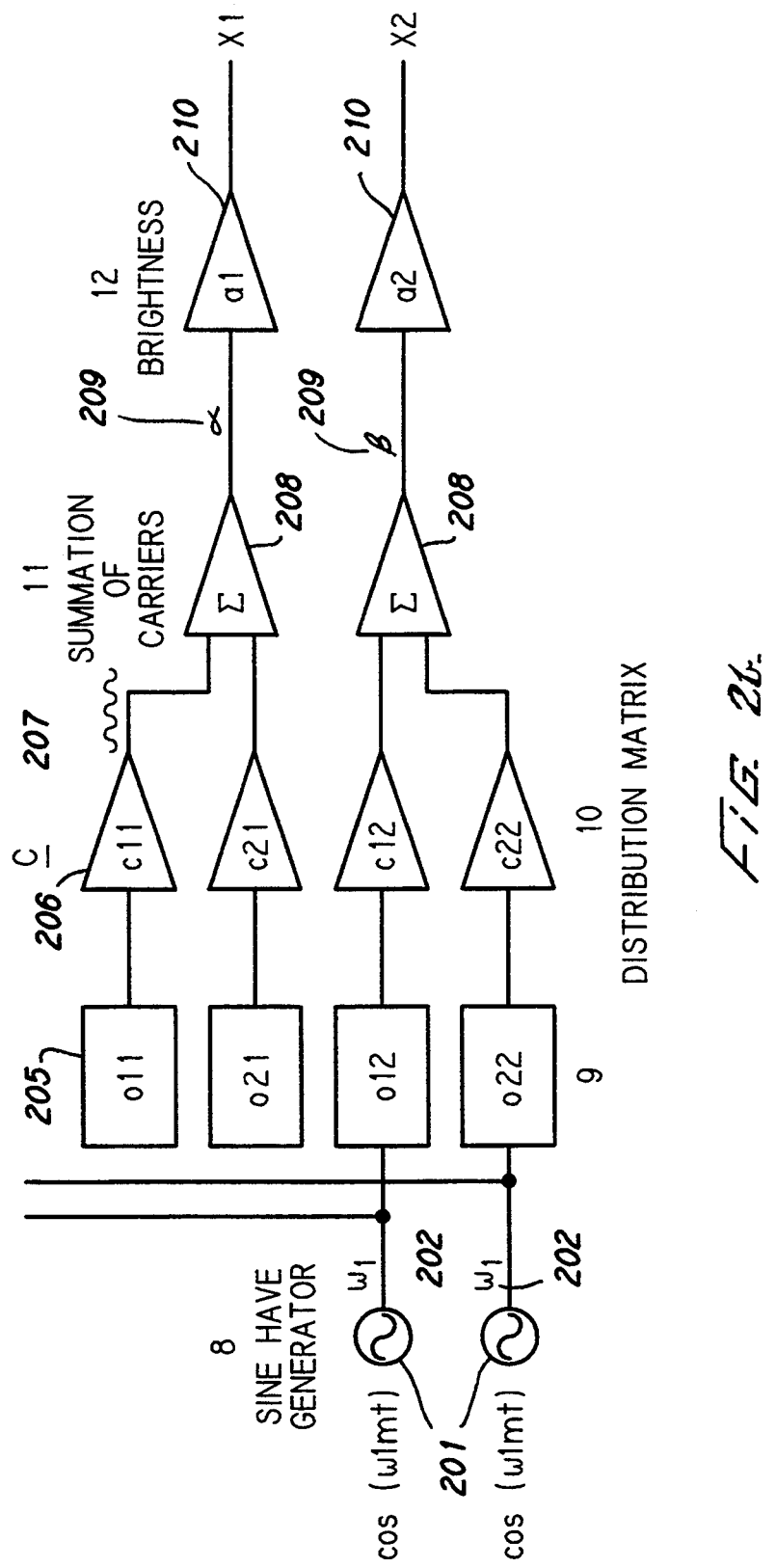
FIG. 2 shows a block diagram of the component-amplitude-division multiplexer and demultiplexer of an embodiment of the invention.

In a preferred embodiment, each of the emitters 101 may comprise an LED (such as part number OPC-8803 made by Marktech International Corp. for the infrared LED and part number MT1500PUR made by Marktech International Corp. for the red LED), as is well known in the art, and may be coupled by means of an LED driver 102, as is well known in the art, to a carrier output 103 of a mux/demux circuit 104 (see FIG. 2).

Energy from the emitters 101 is applied to a tissue section 105 of a patient. In a preferred embodiment for measuring blood oxygen, the tissue section 105 is preferably chosen such that energy from the emitters 101 passes through the patient's blood vessels, such as an end of the patient's finger, the patient's earlobe, or (for neonates) the patient's hand or foot. The tissue section 105 may modulate the energy from the emitters 101, as is well known in the art, e.g., by absorbing some of the energy at each wavelength. Typically, energy may be modulated by transmission through the tissue section 105, but it may occur that energy may be modulated by reflection or by other means.

A detector 106 receives energy after modulation by the tissue section 105 and generates an output signal which indicates the total energy received. In a preferred embodiment, the detector 106 may comprise a photodiode (such as part number OSI-1140 made by Opto Sensors, Inc.), as is well known in the art. An output of the detector 106 is amplified by an amplifier 107 and coupled by means of a filter 108 to a detector input 109 of the mux/demux circuit 104.

The mux/demux circuit 104 generates a data output signal 110 at a data output 111, for each energy wavelength, which indicates the modulation which the tissue section 105 applied to that energy wavelength. In a preferred embodiment for measuring blood oxygen, information such as blood oxygen concentration may be calculated from the output signal, as is well known in the art.

Component-Amplitude-Division Multiplexing

Component-amplitude-division multiplexing ("CADM"), as used herein, is defined as follows. In CADM, a plurality of carrier signals are constructed, each of which may comprise a mixture of carrier components. Each carrier signal may be separately modulated, and the resultants summed. Thereafter, the separate modulations may be recovered from the sum, as disclosed herein.

Thus, a first carrier $\alpha$ may comprise a mixture of two carrier components $\alpha1$ w1+$\alpha2$ w2, while a second carrier $\beta$ may comprise a different mixture of the same two carrier components $\beta1$ w1+$\beta2$ w2. Alternatively, $\alpha$ may comprise a mixture of three components $\alpha1$ w1+$\beta2$ w2+$\alpha3$ w3, while $\beta$ may comprise a different mixture of the same three components $\beta1$ w1+$\beta2$ w2+$\beta3$ w3.

The following relations describe construction of each carrier when the number of carrier components (m) and the number of carrier signals (n) both equal 2, i.e. m=n=2:

$$\begin{bmatrix} \alpha1 & \alpha2 \\ \beta1 & \beta2 \end{bmatrix} \begin{bmatrix} w1 \\ w2 \end{bmatrix} = \begin{bmatrix} \alpha \\ \beta \end{bmatrix} \quad (112)$$

or $$K\Omega = C \quad (113)$$

where K is a matrix of mixing factors $\alpha1$, $\alpha2$, $\beta1$ $\beta2$; $\Omega$ is a vector of carrier components w1, w2; and C is a vector of carrier signals $\alpha$, $\beta$ Applying these relations to the case where m=n>2 would be clear to one of ordinary skill in the art, after perusal of the specification, drawings and claims herein.

The following relation describes separate modulation of each carrier signal:

$$m1\alpha + m2\beta = \sigma \quad (114)$$

where m1 is a first modulating effect (e.g., at an infrared wavelength); m2 is a second modulating effect (e.g., at a red wavelength); and is a detected sum of the modulated carrier signals The detected sum $\sigma$ may be decomposed into separate parts for each carrier component w1, w2:

$$\sigma = m1(\alpha1 w1 + \alpha2 w2) + m2(\beta1 w1 + \beta2\ w2) \quad (115)$$

or $$\sigma = t1\ w1 + t2\ w2 \quad (116)$$

$$t1 = m1\ \alpha1 + m2\ \beta1 \quad (117)$$

$$t2 = m1\ \alpha2 + m2\ \beta2 \quad (118)$$

or $$\begin{bmatrix} \alpha1 & \alpha2 \\ \beta1 & \beta2 \end{bmatrix} \begin{bmatrix} m1 \\ m2 \end{bmatrix} = \begin{bmatrix} t1 \\ t2 \end{bmatrix} \quad (119)$$

or $$KM = T \quad (120)$$

where K is the matrix of mixing factors $\alpha1$, $\alpha2$, $\beta1$, $\beta2$; M is a vector of modulation effects m1, m2; and T is a vector of modulated carrier component parts t1, t2

Separate components may be demultiplexed by multiplying by the left multiplicative inverse of the mixing matrix K:

$$M = K^{-1}T \quad (121)$$

or $$M = K^{-1}KM \quad (122)$$

The mixing matrix K should have a left multiplicative inverse. It would be clear to one of ordinary skill in the art, after perusal of the specification, drawings and claims herein, that K=I, the identity matrix, and even K≈I, would be workable, and are within the scope and spirit of the invention. However, as used herein, a mixing matrix K differs from I. Also, it is generally preferable that I differs substantially from I.

Error Detection and Correction

The following relations describe construction of each carrier when the number of carrier components (m) >the number of carrier signals (n), which equals 2, i.e. m>n=2:

$$\begin{bmatrix} \alpha1 & \alpha2 & \alpha3 \\ \beta1 & \beta2 & \beta3 \\ z1 & z2 & z3 \end{bmatrix} \begin{bmatrix} w1 \\ w2 \\ w3 \end{bmatrix} = \begin{bmatrix} \alpha \\ \beta \\ z \end{bmatrix} \quad (123)$$

or $$K\Omega = C \quad (124)$$

where K is the matrix of mixing factors $\alpha1$, $\alpha2$, $\alpha3$, $\beta1$, $\oplus2$, $\beta3$, z1, z2, z3; is the vector of carrier components w1, w2, w3; and C is the vector of carrier signals $\alpha$, $\oplus$, z An additional row z1, z2, z3 has been added to K to preserve its invertability, and an additional element z has been added to C as a result. Because no carrier signal z is actually used, the row z1, z2, z3 may be chosen arbitrarily, so long as K remains invertible. Of course, the value of $K^{-1}$ depends upon the selection of the row z1, z2, z3.

Because the row z1, z2, z3 may be chosen arbitrarily, $K^{-1}$ may be computed more than once, using more than one row z1, z2, z3. Thus, there will be Ka, using z1a, z2a, z3a, with $K^{-1}a$ Kb, using z1b, z2b, z3b, with $K^{-1}b$, and Kc, using z1c, z2c, z3c, with $K^{-1}c$. Ka, Kb and Kc may each be used to compute M. By comparing the resultant elements of M generated using Ka, Kb, and Kc, interference in one or more carrier components w1, w2, w3 may be detected. Errors may be corrected by majority voting the resultant elements of M.

Applying these relations to the case where $m > n > 2$ would be clear to one of ordinary skill in the art, after perusal of the specification, drawings and claims herein.

Multiplexer/Demultiplexer Circuit

FIG. 2 shows a block diagram of the component-amplitude-division multiplexer and demultiplexer of an embodiment of the invention.

A carrier component generator 201 generates a plurality of carrier components 202 w1, w2. In a preferred embodiment part of each carrier component 202 w1, w2 is allocated to each emitter wavelength. Also, in a preferred embodiment, each carrier component 202 w1, w2 may comprise a sine wave, as follows:

$$w1 = \cos(2\pi f1\, t) \quad (203)$$

$$w2 = \cos(2\pi f2\, t) \quad (204)$$

where f1, f2 are frequencies

In a preferred embodiment, f1 and f2 are chosen such that interference from noise sources, such as ambient light and electromagnetic interference, is minimized. In a preferred embodiment, f1 and f2 are also chosen such that a bandwidth of about 4 Hz for the modulating effects m1, m2 is allowed. Frequencies in the range of about 10–50 Hz are preferred, but it would be clear to one of ordinary skill in the art, after perusal of the specification, drawings and claims herein, that other frequencies would be workable, and are within the scope and spirit of the invention.

It would also be clear to one of ordinary skill in the art, after perusal of the specification, drawings and claims herein, that there is no requirement that w1, w2 must be sine waves. Other types of carrier components 202, such as square waves or other waveforms, would be workable, and are within the scope and spirit of the invention.

It would also be clear to one of ordinary skill in the art, after perusal of the specification, drawings and claims herein, that the invention may be adapted to measurement of other constituents, such as blood carbon dioxide, blood carbon monoxide, other blood gas concentrations, blood glucose, or more generally, other chemical and/or physical concentrations.

It would also be clear to one of ordinary skill in the art, after perusal of the specification, drawings and claims herein, that the choice of $m = n = 2$ is particular to measurement of blood oxygen, and that other choices of m, n would be workable, and are within the scope and spirit of the invention. For example, it may occur that other choices of m, n may be useful, such as for measuring blood carbon dioxide, blood carbon monoxide, other blood gas concentrations, blood glucose, or more generally, other chemical and/or physical concentrations.

Each carrier component 202 w1, w2 is coupled by means of a phase delay 205 to a coefficient amplifier 206 for multiplying by a coefficient of the mixing matrix K, to produce a mixing product 207. The mixing products 207 are summed by a plurality of mixing summing circuits 208 to produce a plurality of carrier signals 209 $\alpha$, $\beta$. This is the matrix multiplication shown in equation 113, 120.

Each carrier signal 209 $\alpha$, $\beta$ is coupled by means of a brightness amplifier 210, for adjusting the brightness of a corresponding emitter 101, to the corresponding carrier output 103 of the mux/demux circuit 104.

The detector input 109 is hetrodyned, as is well known in the art, with the complex carrier components 202 w1, w2 to restore each of the modulated carrier components 202 w1, w2 to baseband. The detector input 109 is coupled to an input of each of a plurality of hetrodyne elements 211. A second input of each of the hetrodyne elements 211 is coupled to one of the carrier components 202 w1, w2, phase-shifted for a real or an imaginary part, as is well known in the art. The phase-shifted carrier components 202 w1, w2 are multiplied to produce a set of complex (real and imaginary) components 212 of each of the carrier components 202 w1, w2, as is well known in the art.

The complex components 212 are coupled to a baseband filter 213, which removes all components except complex baseband components 214. The complex baseband components 214 are coupled to a vector magnitude computer 215, which computes a vector magnitude 216 of the complex baseband components 214.

The vector magnitude 216 is coupled to an inverse coefficient amplifier 217 for multiplying by coefficients of the inverse mixing matrix $K^{-1}$, to produce an inverse mixing product 218. The inverse mixing products 218 are summed by a plurality of inverse mixing summing circuits 219 to produce the data output signals 110. This is the matrix multiplication shown in equation 121.

The data output signals 110 each indicate the product of the modulation effect for the corresponding carrier signal 209 w1, w2, as multiplied by a correction by the corresponding brightness amplifier 210. Each data output signal 110 is coupled to the corresponding data output 111 of the mux/demux circuit 104.

In a preferred embodiment, signal generation and signal manipulation as described herein are preferably performed by a digital microprocessor (such as part number DSP56001 made by Motorola) operating under software control. It would be clear to one of ordinary skill in the art, after perusal of the specification, drawings and claims herein, that programming a standard digital microprocessor to perform signal generation and signal manipulation as described herein would be a straightforward task and would not require undue experimentation.

It would be clear to one of ordinary skill in the art, after perusal of the specification, drawings and claims herein, that the invention may be combined with known methods of computing blood oxygen concentration and other blood gas values from the data output signals 110 which are produced. Providing a system which combines the invention with such known methods would be a straightforward task, after perusal of the specification, drawings and claims herein, and would not require undue experimentation.

Alternative Embodiments

While preferred embodiments are disclosed herein, many variations are possible which remain within the concept and scope of the invention, and these variations would become clear to one of ordinary skill in the art after perusal of the specification, drawings and claims herein.

We claim:

1. A device for collecting photoplethysmographic data, comprising
    means for multiplying a mixing matrix and a vector of component signals;
    means for applying a plurality of modulating effects to a resultant of said means for multiplying; and
    means for multiplying an inverse of said mixing matrix and a resultant of said means for applying.

2. A device as in claim 1, comprising means for determining, in response to a set of photoplethysmographic data, blood gas data.

3. A device as in claim 1, comprising means for determining, in response to a set of photoplethysmographic data, at least one of blood oxygen, blood carbon dioxide, or blood carbon monoxide.

4. A device as in claim 1, wherein said means for multiplying a mixing matrix comprises means for multiplying a square matrix.

5. A device as in claim 1, wherein said means for multiplying a vector of component signals comprises means for multiplying at least one component signals which comprises a sum of at least one of a sine wave, or a square wave.

6. A device as in claim 1, wherein said means for applying comprises a plurality of light-emitters.

7. A device as in claim 1, wherein said means for applying comprises a plurality of light-emitters tuned to a plurality of wavelengths.

8. A device as in claim 1, wherein said means for applying comprises means for directing said resultant at a modulating medium.

9. A device as in claim 1, wherein said means for applying comprises means for directing said resultant at animal tissue.

10. A device as in claim 1, wherein said means for applying comprises means for directing said resultant at a modulating medium comprising at least one of blood, blood vessels, bone marrow, ligament, muscle, or skin.

11. A device as in claim 1, comprising
    means for detecting a composite resultant of said means for applying; and
    means for separating said composite resultant into a vector resultant.

12. A device as in claim 11, wherein said means for separating comprises at least one heterodyning element.

13. A device as in claim 11, wherein said means for detecting a composite resultant comprises means for detecting a sum of at least two elements of said vector resultant.

14. A device as in claim 1, wherein said means for applying comprises means for directing said resultant at animal tissue.

15. A device as in claim 1, wherein said means for applying comprises means for directing said resultant at a modulating medium comprising at least one of blood, blood vessels, bone marrow, ligament, muscle, or skin.

16. A device as in claim 1, wherein said means for applying a plurality of modulation effects comprises means for applying at least one amplitude modulation effect.

17. A device as in claim 1, wherein said means for applying a plurality of modulating effects comprises means for applying an amplitude modulation effect which varies with energy wavelength.

18. A device as in claim 1, wherein said means for applying a plurality of modulating effects comprises means for applying at least one modulating effect with a time-varying component.

19. A device as in claim 1, wherein said means for applying a plurality of modulating effects comprises means for applying at least one modulating effect with a time-varying component which is correlated with a biological process.

20. A device as in claim 1, wherein said means for applying a plurality of modulating effects comprises means for applying at least one modulating effect having a transmission response of a modulating medium.

21. A device for collecting photoplethysmographic data, comprising
    means for component-amplitude-division multiplexing a plurality of modulating signals;
    means for applying a modulation effect to a resultant of said means for component-amplitude-division multiplexing; and
    means for component-amplitude-division demultiplexing said plurality of signals;
    wherein said means for component-amplitude-division multiplexing and said means for component-amplitude-division demultiplexing collectively comprise means for multiplying a mixing matrix and means for multiplying an inverse of said mixing matrix.

22. A device for collecting photoplethysmographic data, comprising
    means for component-amplitude-division multiplexing a plurality of modulating signals;
    means for applying a modulation effect to a resultant of said means for component-amplitude-division multiplexing; and
    means for component-amplitude-division demultiplexing said plurality of signals;
    and means for error detection in response to a resultant of said means for component-amplitude-division demultiplexing.

23. A device as in claim 22, wherein said means for error detection comprises means for generating a plurality of carrier signals using a number of carrier components in excess of a number of carrier signals.

24. A device as in claim 22, wherein said means for error detection comprises means for multiplying a plurality of mixing matrices.

25. A device for collecting photoplethysmographic data, comprising
    means for component-amplitude-division multiplexing a plurality of modulating signals;
    means for applying a modulation effect to a resultant of said means for component-amplitude-division multiplexing; and
    means for component-amplitude-division demultiplexing said plurality of signals;
    and means for error correction in response to a resultant of said means for component-amplitude-division demultiplexing.

26. A device as in claim 25, wherein said means for error correction comprises means for majority voting a resultant of component-amplitude-division multiplexing and demultiplexing with a plurality of mixing matrices.

27. A method of collecting photoplethysmographic data, comprising the steps of
multiplying a mixing matrix and a vector of component signals;
applying a plurality of modulating effects to a resultant of said step of multiplying; and
multiplying an inverse of said mixing matrix and a resultant of said step of applying.

28. A method as in claim 27, wherein said step of applying comprises the step of directing said resultant at animal tissues.

29. A method as in claim 27, wherein said step of applying comprises the step of directing said resultant at a modulating medium comprising at least one of the group: blood, blood vessels, bone marrow, ligament, muscle, skin.

30. A method as in claim 27 wherein comprising determining blood gas data in response to a resultant of said step of multiplying an inverse.

31. A method as in claim 27, comprising determining at least one of blood oxygen, blood carbon dioxide, or blood carbon monoxide.

32. A method as in claim 27, wherein said mixing matrix is a square matrix.

33. A method as in claim 27, wherein at least one of said component signals comprises a sum of at least one of a sine wave, or a square wave.

34. A method as in claim 27, wherein at least one of said modulating effects comprises amplitude modulation.

35. A method as in claim 27, wherein said modulating effects comprise an amplitude modulation effect which varies with energy wavelength.

36. A method as in claim 27, wherein at least one of said modulating effects comprises a time-varying component.

37. A method as in claim 27, wherein at least one of said modulating effects comprises a time-varying component which is correlated with a biological process.

38. A method as in claim 27, wherein at least one of said modulating effects comprises at least one transmission response of a modulating medium.

39. A method as in claim 27, comprising the steps of detecting a composite resultant of said step of applying; and
separating said composite resultant into a vector resultant.

40. A method as in claim 39, wherein said step of separating comprises at least one hetrodyning step.

41. A method as in claim 39, wherein said composite resultant comprises a sum of at least two elements of said vector resultant.

42. A method of collecting photoplethysmographic data, comprising the steps of
component-amplitude-division multiplexing a plurality of modulating signals;
applying a modulation effect to a resultant of said means for component-amplitude-division multiplexing; and
component-amplitude-division demultiplexing said plurality of signals;
and performing of error detection in response to a resultant of said step of component-amplitude-division demultiplexing.

43. A method of collecting photoplethysmographic data, comprising the steps of
component-amplitude-division multiplexing a plurality of modulating signals;
applying a modulation effect to a resultant of said means for component-amplitude-division multiplexing; and
component-amplitude-division demultiplexing said plurality of signals;
and performing error correction in response to a resultant of said step of component-amplitude-division demultiplexing.

44. A method as in claim 43, wherein said step of error correction comprises majority voting a resultant of component-amplitude-division multiplexing and demultiplexing with a plurality of mixing matrices.

* * * * *